United States Patent [19]

Williams et al.

[11] Patent Number: 4,869,286

[45] Date of Patent: Sep. 26, 1989

[54] FLUID INJECTION SYSTEM COUPLING AND INJECTOR VALVE

[75] Inventors: Harold R. Williams, Capistrano Beach; Robert M. Spencer, San Juan Capistrano, both of Calif.

[73] Assignee: Surgikos, Inc., Arlington, Tex.

[21] Appl. No.: 185,747

[22] Filed: Apr. 25, 1988

Related U.S. Application Data

[62] Division of Ser. No. 52,721, May 20, 1987, abandoned.

[51] Int. Cl.$^4$ .................. F16K 15/14; F16K 51/00
[52] U.S. Cl. .................. 137/318; 137/510; 137/613; 251/61.1; 422/81; 422/103
[58] Field of Search ............. 137/510, 859, 318, 613; 222/80, 81, 82; 422/103 X, 81 X; 251/61.1

[56] References Cited

U.S. PATENT DOCUMENTS

| | | | |
|---|---|---|---|
| 3,024,044 | 3/1962 | Benevento | 137/318 X |
| 3,521,850 | 7/1970 | German | 251/61.1 X |
| 3,554,217 | 1/1971 | Ehrens | 137/318 |
| 3,999,528 | 12/1976 | Knapp et al. | 137/510 X |
| 4,134,940 | 1/1979 | Sherman | 137/318 X |
| 4,177,828 | 12/1979 | Vache | 137/318 |
| 4,243,070 | 1/1981 | Jackson | 137/859 X |
| 4,753,570 | 6/1988 | Jarvis | 137/510 X |

FOREIGN PATENT DOCUMENTS 44228 1/1966 German Democratic Rep. .

Primary Examiner—Stephen Hepperle
Attorney, Agent, or Firm—Joseph F. Shirtz

[57] ABSTRACT

A cassette containing a group of sealed cells is used as a means for delivering doses of fluid to be injected into a sterilizing chamber. After the cassette is automatically positioned over a piercing mechanism, the cassette is moved downwardly so that a cell is pierced. Fluid is then forced out of the cell by pneumatic pressure into an injector valve, which opens in a manner which does not adversely affect a vacuum within the chamber.

5 Claims, 5 Drawing Sheets

FLUID INJECTION SYSTEM COUPLING AND INJECTOR VALVE

This is a division of application Ser. No. 052,721, filed May 20, 1987 now abandoned.

FIELD OF THE INVENTION

The present invention relates to a system for injecting or dispensing controlled volumes of fluid, the system being particularly useful for automated injections of very small amounts of fluid into a sterilizing chamber for items such as medical instruments.

BACKGROUND OF THE INVENTION

U.S. Pat. No. 4,643,876 discloses a sterilization system in which an agent such as hydrogen peroxide is introduced into an evacuated sterilizing chamber wherein it is vaporized and allowed to disperse onto the items to be sterilized. After a desired period of time, electrical energy is then applied in the chamber to ionize the gas to form a plasma at a power level sufficient to achieve sterilization. These steps can be performed in different chambers.

The system is proving to be very effective, and also has a number of advantages over other known systems. Consequently, the system is being commercialized and a need exists for apparatus providing the proper quantity of the desired fluid in a safe, convenient and practical manner. Also, an injection system must perform its function accurately and reliably without providing a leak path for the introduction of unwanted air or other material to the sterilizing chamber. In addition to preventing leaks, the accuracy requirement includes the need for minimizing the volume of fluid that remains in the system between injections.

When the system is used with sterilizing apparatus in a medical environment such as in a hospital, it is likely to be operated on a repeated basis throughout the day by personnel having a widely varying range of understanding of the apparatus employed. Hence, it is important that the system be simple to operate, be fully automated and have adequate safeguards with respect to human error in view of the critical nature of sterilization of medical items. Minimizing the chance of human error is thus important. Also, the apparatus must have adequate reliability for heavy usage of the apparatus over an extended period of time.

Prior fluid injection systems in sterilizing apparatus do not provide the desired features. In one known system, ethylene oxide gas is sealed under its own pressure in a container and then dispensed as needed. This approach is not practical with a liquid delivery system in that a gaseous propellant contained in the liquid is not acceptable in the sterilizing process. Also, delivery pressure decays during the delivery process, which can result in an undelivered dead volume, and degradation in the quality of atomization of the fluid as it enters the chamber.

Thus, need exists for an improved system.

SUMMARY OF THE INVENTION

The entire improved system is disclosed herein, however, only the injector valve and fluid inlet structure are claimed. Briefly stated, the invention comprises a fluid coupling and injector valve assembly for use in a fluid injection system. The valve includes a lower housing section having an annular valve seat leading to an outlet passage through the section and having a recess in said section around said valve seat forming an inlet passage. A flexible valve element, such as a flat diaphragm, extends over the valve seat to control flow through the valve seat and to cover the inlet recess such that fluid pressure in the recess biases the flexible element away from the valve seat to allow fluid flow from the inlet passage into a valve outlet passage. A mating upper valve housing section cooperates with the lower section to clamp the flexible element in position, and a spring urges the valve element into a normally closed position with respect to the valve seat. With this arrangement, when the valve outlet passage is in communication with a vacuum chamber, the valve maintains the vacuum in the chamber and only opens briefly as fluid is being injected out of the valve. Moreover, the vacuum applied to the outlet of the valve also produces a closing force on the valve.

The recess in the lower valve section has an annular shape and is very shallow, but yet extends a considerable distance radially. With this arrangement, a significant valve opening force is generated with a very small volume of fluid. This is important in that it maintains the volumetric accuracy of the fluid doses which are metered out of the valve in that only a very small portion of a fluid dose remains in the valve. Of course, this small amount only affects the first injection.

Also mounted on the upper housing section is a further valve inlet passage formed by a small diameter conduit, in a floating seal assembly. The conduit forms the inlet passage to the valve and communicates with the recess surrounding the valve inlet by way of a small hole through a peripheral portion of the valve element. A tubular seal member is slideably mounted on the upper portion of the conduit to form a seal with a mating fluid cell which is pierced by a sharp upper end of the conduit. The seal member is spring mounted to maintain a seal between the seal member and the component during the piercing of the cell and the forcing of fluid out of the cell.

Further, the lower part of the seal member includes an inner annular portion which seals with the exterior of the conduit. The face of the lower end engages the upper end of a tubular follower, and the engaging surfaces are formed so that under the bias of a spring there is provided an inward force on the annular portion to maintain the seal.

Other features of the fluid injection system are claimed in related copending applications.

DETAILED DESCRIPTION OF THE PREFERRED EMBODIMENT

Figure 1:
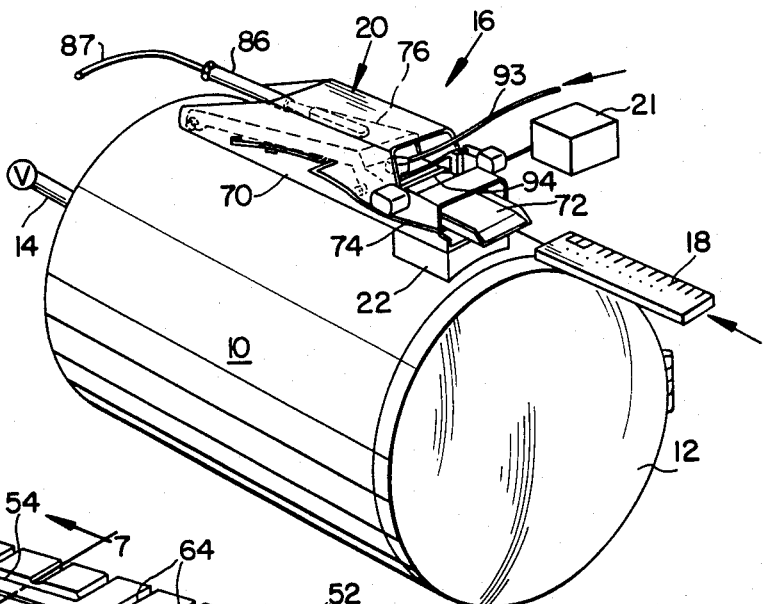
FIG. 1 is a perspective, somewhat schematic view of sterilizing apparatus illustrating the system of the invention.

Referring to FIG. 1, there is schematically illustrated a cylindrical chamber 10 having a door 12 on one end. The chamber is connected to a suitable vacuum source by way of a conduit 14. The chamber is adapted to receive items to be sterilized, such as surgical instruments, in accordance with a method outlined in the above-referenced patent, wherein a liquid such as hydrogen peroxide is introduced into the chamber. For delivering such fluid, in accordance with the present invention, there is provided a fluid injection system 16 positioned adjacent to the chamber 10.

The system includes a cassette or cartridge 18 containing the fluid to be injected, a cassette receiving, positioning and clamping mechanism 20, and a fluid injector valve assembly 22 mounted on and interconnected with the chamber. The fluid injector system 16 can be thought of as a pump in which the cassette 18 is inserted into the cassette receiving mechanism 20 and doses of the media contained in the cassette are automatically injected into the chamber during automated sterilizing cycles.

Cassette

The cassette 18 is in the form of a flat, rectangular rigid structure preferably made of plastic or other suitable material. The form of the cassette illustrated includes an upper housing section 24 which mates with the lower section 26 to capture and enclose a cell strip assembly 28 or cell pack. The sections are held together by fasteners or other suitable means. The pack assembly has a rectangular shape, with slightly smaller dimensions than that of sections 24 and 26 such that the pack fits within the confines of the outer sections, as may be seen from FIG. 7.

The cell pack includes a plurality of fluid cells 30 arranged in the form of two rows of spaced cells with the cells of one row being offset in a lengthwise direction from the cells of the adjacent row and partially positioned between the cells of the adjacent row. Such an arrangement provides ten cells in the example shown in a compact space. When considering the sequence of the cells in the longitudinal direction of the assembly, this places the first cell in one row and the second cell in the other row, etc.

Figure 5:
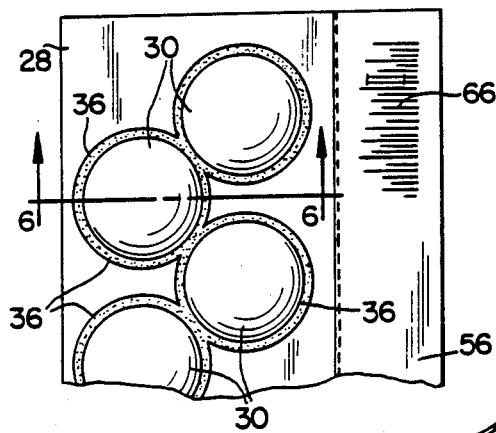
FIG. 5 is a top plan view of the forward end of the cell pack of FIG. 4.
Figure 6:
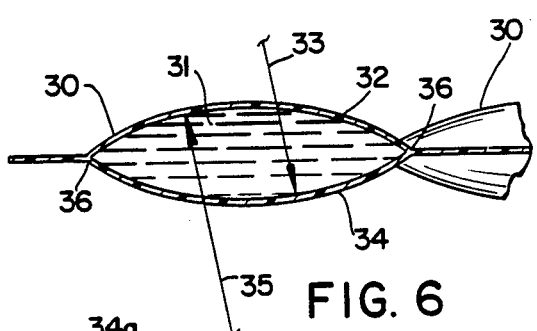
FIG. 6 is a cross-sectional view on the line 6—6 of FIG. 5.

As seen from FIGS. 5 and 6, each cell is formed by a pair of flexible walls including a delivery wall or side 34 and a pressure wall or side 32. As seen from FIG. 5, these walls have a spherical exterior and are bonded together around their periphery, forming a joint or seam 36. These walls 32 and 34 are preferably each formed or molded in a plastic sheet on a spherical radius. The radius 35 of the pressure side 32 is slightly smaller than the radius 33 of the delivery side 34 in an amount equal to the formed film thickness so that the pressure side will nest perfectly into the delivery side when the cell is emptied. This contributes to the accuracy of the amount of fluid delivered and avoids dead volume. The cells are filled with liquid 31 of a precisely known volume. Advantageously, the liquid is unpressurized in the cell such that volumetric accuracy is simplified, as are leakage problems. Preferably, cell filling is done in conjunction with the operation of bonding the peripheries of the layers of the cell. In the example of the sterilizing method referred to in the above-referenced patent, the liquid sealed within the cell is hydrogen peroxide but, of course, other materials can be used; and the cassette and cell structure is useful for delivering fluid in connection with operations other than in connection with sterilizing apparatus.

The lower cassette section 26 is formed with a plurality of walls 38 forming a plurality of internally facing spherical recesses 39 matching the shape of the delivery side 34 of a cell 30. The cassette upper section 24 is formed with a plurality of circular walls 40 which, in cooperation with the walls 38, form a plurality of circular compartments 42 each of which confines a cell 30. The lower section has a flat annular wall surface 44 surrounding the recess 39 which with the lower circular edge of the wall 40 securely holds the cell bonded joint 36 to seal the compartment 42 in that area. The recess 39 is likewise sealed in this manner. The pliability of the plastic material forming the joint 36 assists in forming a seal. If the material forming the cell pack is not adequately pliable or resilient, a suitable gasket may be added.

As may be seen, the pressure side 32 of a cell is spaced from the flat wall of the upper housing section 24 so that a space or pressure cavity is formed thereby. The pressure side of each compartment 42 is formed with an aperture 46 that interconnects the compartment 42 with the exterior of the cassette. Ten of these apertures 46 may be seen in FIG. 2. Each aperture 46 is located near the periphery of its compartment 42 on the side of the compartment that is adjacent to the other row of cells and compartments. This arrangement creates a single row of apertures 46.

The row of apertures 46 is covered by an indicator strip 47 having a lower layer 47a which engages the cassette surface and is exposed on one side to the compartment 42. This lower layer 47a is treated chemically such that if it is exposed to hydrogen peroxide, it will change color, thus indicating that the cell 30 in that compartment is leaking. Of course, if material other than hydrogen peroxide is confined in the cell, the layer 47a will be treated with an appropriate material which will indicate the presence of that fluid. An upper layer 47b is a film of plastic to protect the indicator layer 47a from material other than the fluid in the cell and to trap any fluid that has escaped.

The lower cassette section 26 is formed with a hole 49 which is centrally positioned in the recess 39 and with respect to the cell 30 in the compartment 42. This creates two rows of holes 49 which may be seen in FIG. 3. In addition, there is formed a socket 50 in the lower housing section 26, spaced laterally from each hole 49, thus positioning such socket between a pair of compartments in the adjacent row. Since a similar socket 50 is laterally aligned with the hole in each socket, this creates two rows of sockets 50, each aligned with a row of holes 49, as may be seen from FIG. 3. These sockets extend inwardly about half way into the cassette, the socket upper surface, as viewed in FIG. 7, being approximately flush with the annular wall 44 surrounding each compartment.

Figure 2:
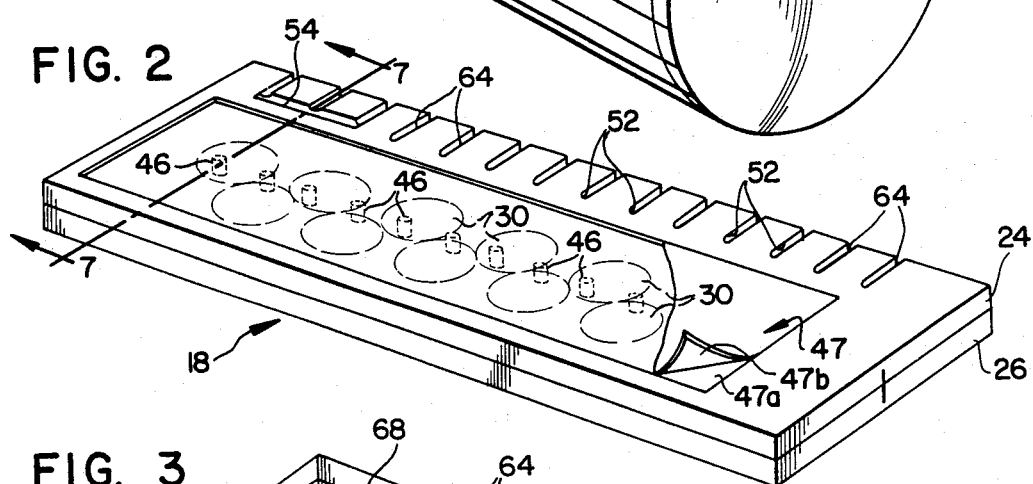
FIG. 2 is a top perspective view of the cassette or cartridge of FIG. 1 containing the fluid to be dispensed.
Figure 7A:
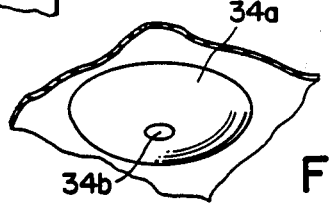
FIG. 7a is a fragmentary perspective view of an alternative construction for a portion of a cassette.
Figure 7:
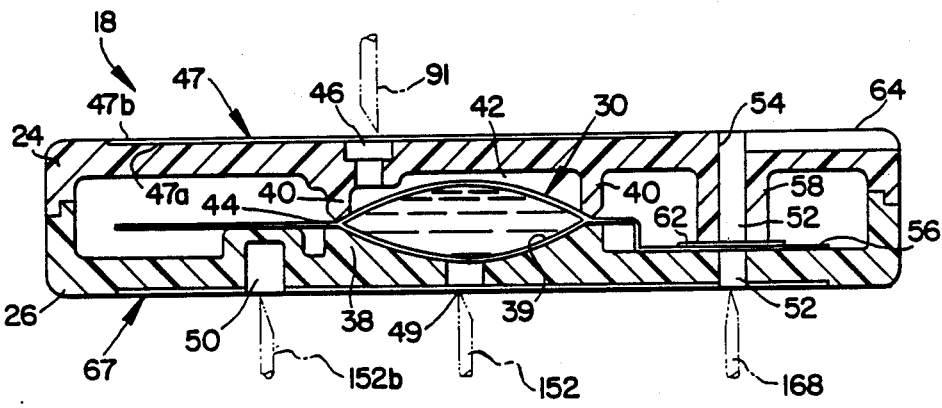
FIG. 7 is a cross-sectional view of the cassette on line 7—7 of FIG. 2.

Both cassette sections are formed with a plurality of aligned openings 52 arranged in a row that extends parallel to the longitudinal edge of the cassette, spaced inwardly a short distance from the right edge, as viewed in FIGS. 2 and 7. Also formed in this same row is a slot 54 that extends through both sections. The slot is at the entry end of the cassette at the end of the row of openings 52. A transparent edge portion 56 of the cell pack intersects the openings 52 and the slot 54. More specifically, the upper cassette section 24 is formed with a series of projecting wall portions 58 which define the portions of the slot 54 and openings 52 which are in the upper section. These projections 58 engage the strip portion 56 and capture it against the inner surface of the cassette lower section 24.

A layer of foil 62 is positioned on the plastic sheet 56 in that location and may be seen through transparent plastic. The foil is perforated as an indicator when an associated cell 30 is used, as will be described below.

The cassette is further formed with a plurality of spaced grooves 64 on one edge of the upper surface of the cassette upper section 24, the grooves being transversely aligned with the openings 52 and extending from the openings to the edge of the cassette. The spacing between the grooves and between the openings is equal to the spacing between the apertures 46 and holes 49 in the cassettes. There is a groove 64 transversely aligned with each compartment 42. However, it is not necessary that they be aligned; only that one groove is associated with each compartment, and that an offset (if any) is constant. In addition, there is a groove on the entry end of the cassette which is spaced forwardly from the first compartment, and three grooves on the trailing end of the cassette which extend beyond the last compartment 42. In the particular system disclosed, the first two and the last one groove are included for aesthetic reasons only.

Also positioned on the surface of the cell strip portion 56 is a bar code 66 located at the entry end of the cassette. This bar code which identifies and dates the cell pack is aligned with the slot 54 so that the bar code can be read through the slot. The date is preferably the date the cells were filled with fluid or the safe use expiration date of the fluid.

An indicator strip or label 67 is attached to the lower surface of the cassette and covers the holes 49, as well as the sockets 50, the openings 52 and a portion of the slot 54. A window 69 in the label 67 permits partial viewing of the bar code 66. A strip layer 67a indicates the existence of cell leakage, and a plastic layer 67b seals the area and protects the indicator layer.

Figure 3:
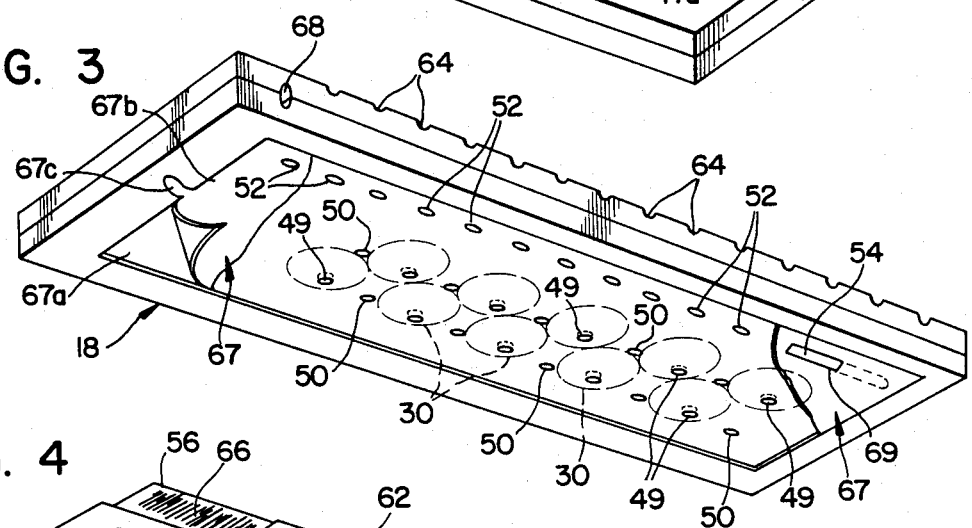
FIG. 3 is a bottom perspective view of the cassette of FIG. 2.
Figure 4:
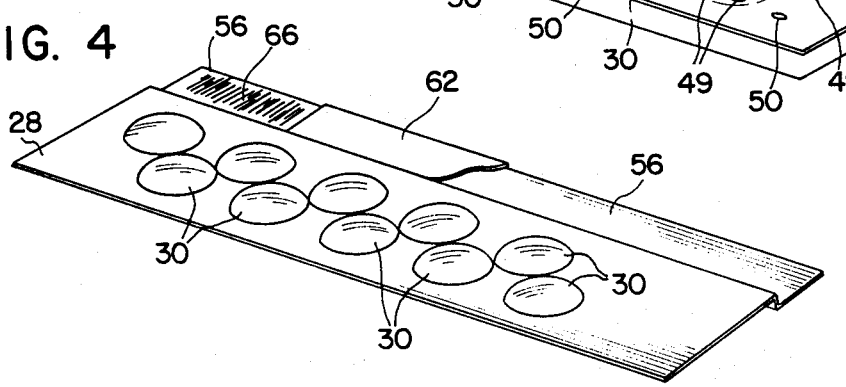
FIG. 4 is a top perspective view of a pack of fluid cells contained within the cassette of FIGS. 2 and 3.

As seen from FIG. 3, there is provided a sensing hole 68 on the edge of the cassette near the trailing end of the cassette. This hole is used as a stop or indicator in connection with the positioning of the cassette in the dispensing mechanism, as to be subsequently described.

The cassette 18 provides a convenient package for presenting measured quantities of the fluid to be dispensed. Although the structure uniquely includes many features, it is inexpensive in mass production, and thus is practical as a disposable item. In addition to providing a convenient vehicle for the fluid to be dispensed, it protects operating personnel from being exposed to fluid in the cassette. Likewise, it presents a safe and protected storage means for the fluid so that it is not contaminated.

Cassette Receiving and Clamping Mechanism

Figure 8:
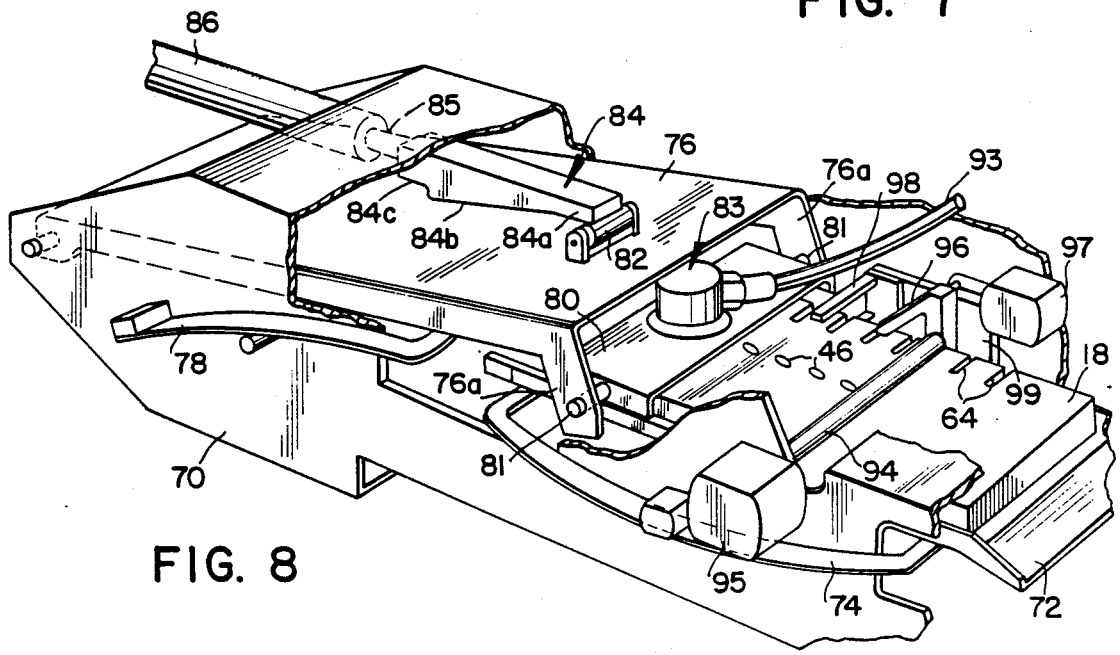
FIG. 8 is a top, perspective, partially cutaway view of the cassette positioning and compressing mechanism of FIG. 1.

The mechanism for receiving a cassette 18 includes an outer hollow frame 70 which is mounted on the sterilizing chamber 10, preferably by being positioned on the injector valve assembly 22, as seen in FIG. 1. Positioned within this frame 70 is a platen 72 which is adapted to receive a cassette 18, as seen in FIGS. 1 and 8. The platen is forced upward by suitable springs 74. A clamping plate 76 is pivoted to the rear portion of the frame 70 and is forced upward by suitable springs 78 so as to create a space with the platen 72 for receiving the cassette 18. A clamp saddle-member 80 straddles a cassette 18 and is pivotally mounted by pins 81 carried on arms 76a depending from the clamping plate.

Positioned on the top side of the clamp plate 76 is a roller 82 which supports the forward end 84a of an elongated cam 84. The cam further includes a central section 84b which slopes downwardly and rearwardly, and a trailing horizontally extending section 84c which is at a lower level than the forward section 84a. The cam is mounted on an actuator rod 85 extending from an actuator housing 86 which in turn is supported on a fixed structure such as the frame 70 by suitable means (not shown). The actuator is in turn connected to a source of pressurized fluid by a conduit 87, as seen in FIG. 1 but, of course, could be energized by other means, such as electric.

On the saddle clamp 80 is a clamp assembly 83 for pressurizing or forcing fluid 31 out of a cell 30. The clamp assembly 83 includes a generally cylindrically shaped clamp 88 which extends through the clamp saddle 80 and includes a flat lower surface adapted to engage the upper surface of a cassette 18. An annular spring element 89 captured in a groove in the clamp 88 extends outwardly and downwardly to react against the top surface of the clamp saddle 80 to hold the clamp 88 in position on the saddle 80. An O-ring 90 positioned within a shallow recess in the face of the clamp 88 extends slightly below the face. A tubular piercing needle 91 is mounted within a passage 92 in the clamp 88, with the piercing tip of the needle extending slightly below the lower surface of the clamp and the O-ring 90. The passage 92 in the housing is in turn connected by a suitable flexible conduit 93 to a source of pressurized air.

To position the cassette 18, there is a provided a drive roller 94 rotatably mounted on the frame 70, which frictionally engages the upper surface of the cassette, the roller being driven by a motor 95 also mounted on the frame 70. For stopping the cassette in proper position with respect to a cell 30, there is provided a spring loaded pawl 96 which cooperates with the grooves 64 on the upper surface of the cassette. The pawl is movable by a solenoid 97 mounted on the frame 70. Also provided is a sensor or detector 98 for reading the bar code 66 in the cassette positioned below a hole (not shown) in the platen 72 to be aligned with the openings 52 and the slot 54 when a cassette is inserted into the mechanism 20. Also positioned on the frame 70 is a detector 99 (not shown in detail) located to observe the edge of the cassette as it moves within the cassette positioning mechanism. A schematically indicated microprocessor 21 connected to the detectors controls the operation of the mechanism 20.

Injector Valve Assembly

Turning now to FIGS. 9, 10, 11 and 12, it may be seen that the injector valve assembly 22 includes a mounting body 100 which is welded or otherwise suitably secured to a wall 11 of the chamber 10. The injector body 100 has a cylindrical interior in which is positioned mating sections 102 and 104 forming a valve body or housing. These sections are clamped together by a spanner nut 106 or other suitable means which threads into the interior of the body 100, with a washer 108 positioned between the nut 106 and an outwardly extending flange on the upper valve housing section 102.

The primary housing section 104 includes a centrally located, upwardly extending annular valve seat 110 surrounding the entry to an elongated valve outlet passage 111 in the primary section that is covered or closed by a large, flat flexible diaphragm 112 which forms a movable, pressure-responsive valve element for controlling flow through the valve. The diaphragm 112 fits within a circular, flat recess 114 formed in the primary housing section 104. The recess 114 is flush with the valve seat 110. Formed in the central portion of the recess 114 is a smaller diameter shallow annular recess 116 surrounding the annular valve seat 110 and forming a portion of an inlet passage to the valve seat 110. The radial dimensions of the recess 116 is quite large relative to its depth such that a large valve opening force is generated with negligible fluid volume. For example, in one form of the invention the recess 116 depth is about 0.007 inch and the recess diameter is about 0.9 inch creating a volume of about 0.004 in$^3$.

Figure 12:
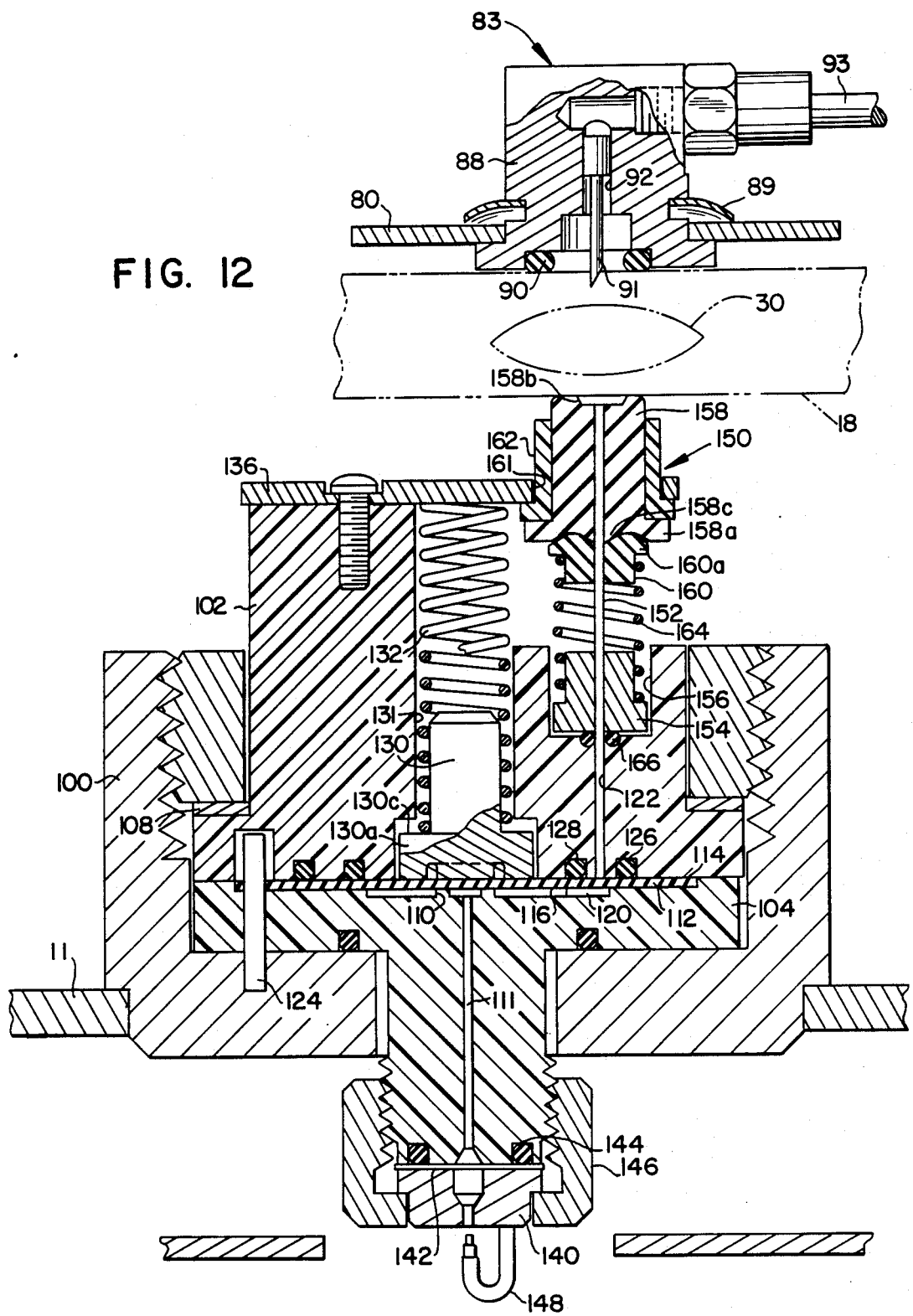
FIG. 12 is a cross-sectional view of the injector valve assembly on line 12—12 of FIG. 11, together with a cross-sectional view of the air delivery system for compressing a fluid cell in the cassette.

Also formed in the lower housing section 104 are a pair of radially extending, circumferentially spaced, shallow passages 120 which open on their radially inner ends to the inlet recess 116. The radially outer ends of these passages are aligned with openings 113 formed in the flexible diaphragm 112 and aligned with small diameter passages 122 extending in an axial direction through the upper valve housing section 102 radially outwardly from the central space 131. A pair of positioning pins 124, shown in FIG. 9 (only one of which is shown in FIG. 12), extend through radially outer portions of the valve housing sections 102 and 104, the outer periphery of the diaphragm 112 and into a socket in the valve assembly body 100. These pins 124 orient the diaphragm 112 in the upper housing section 102 so that the holes in the diaphragm and the passages in the upper housing section are aligned with the radially outer ends of the passage 120. They also align the entire injector body assembly to the cassette receiving mechanism.

An outer O-ring 126, positioned within a groove in the upper housing section 102, seals the valve inlet passage radially outwardly from the passage 122. Correspondingly, an inner O-ring 128 prevents fluid flow between the upper side of the diaphragm 112 and the upper housing section 102.

Positioned on top of the diaphragm 112 is a movable piston 130 located within a suitably formed, centrally located space 131 in the upper housing section 102 which is open to ambient pressure. A lower head portion 130a of the piston 130 engages the top side of the diaphragm 112 opposite from the valve seat 110. A compression spring 132 surrounds an upper cylindrical portion of the piston 130 and reacts against a shoulder 130c to force the piston 130 into valve closing position against the diaphragm 112 and the valve seat 110. The other end of the spring 132 reacts against a retainer plate 136 which is attached by suitable fasteners 138 to the upper end of the upper valve housing section 102.

Positioned on the lower end of the lower valve housing section 104 is an atomizing nozzle 140 clamped against a filter 142 and an O-ring 144 by means of a surrounding sleeve nut 146. An atomizing finger 148 secured to the nozzle 140 is aligned with an opening through the nozzle and with the valve outlet passage 111 to facilitate the atomizing of fluid ejecting from the outlet.

Cell Piercing/Floating Seal Assembly

Still referring to FIGS. 9-12, the injector valve assembly further includes a cell opener assembly or a cell piercing and floating seal assembly 150. The assembly 150 which forms a fluid coupler includes a conduit in the form of a tubular needle 152. The needle is secured to a surrounding needle support member 154 positioned within a socket 156 formed in the upper surface of the upper valve housing section 102. The socket is adjacent to but spaced radially outwardly from the central space 131. The lower portion of the needle fits closely within the inlet passage 122, while the sharp upper end of the needle extends upwardly in position to pierce a fluid cell 30. A resilient tubular seal element 158 having an axial bore therein surrounds the upper portion of the needle 152. A tubular follower 160, made of material more rigid than the seal 158, engages the lower portion of the seal 158. A tubular sleeve or guide 162 surrounds the seal 158 and extends through an opening 161 in the retainer 136. The guide 162 is provided with an outwardly extending flange which engages the lower surface of the plate 136, and the lower surface of this flange engages an outwardly extending flange 158a on the lower end of the seal 158.

A compression spring 164 extends between a flange 160a on the follower 160 and an outwardly extending flange on the lower end of the needle support 154. This spring biases the follower 160, the seal 158 and the guide 162 upwardly against the retainer plate 136. The spring also biases a small O-ring 166 into a groove in the housing section 102 surrounding the needle 152 so as to prevent fluid flow between the passage 122 and the socket 156.

The upper end of the seal 158 includes an upwardly extending annular face portion 158b which engages the lower surface of a cassette 18 to form a seal therewith. The bore within the seal 158 includes an inwardly extending seal portion 158c on its lower end which resiliently engages the exterior of the needle 152 to form a seal at that location. The central protuberance on the lower end of the seal 158 surrounding the portion 158c has a conical shape that fits within a mating conical recess in the upper surface of the follower 160. These mating surfaces, together with the force of spring 164, bias the seal portion 158c into engagement with the needle to form a good sliding seal.

Figure 9:
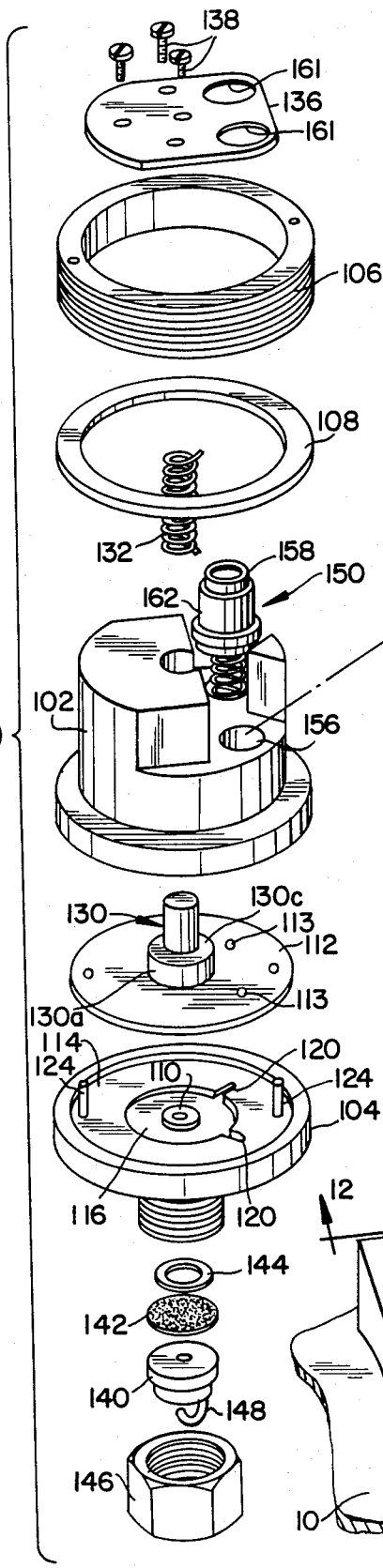
FIG. 9 is an exploded perspective view of the injector valve assembly of the invention.
Figure 10:
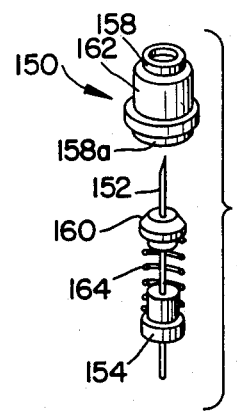
FIG. 10 is an exploded perspective view of the cell piercing and floating seal mechanism which is a portion of the assembly of FIG. 9.
Figure 11:
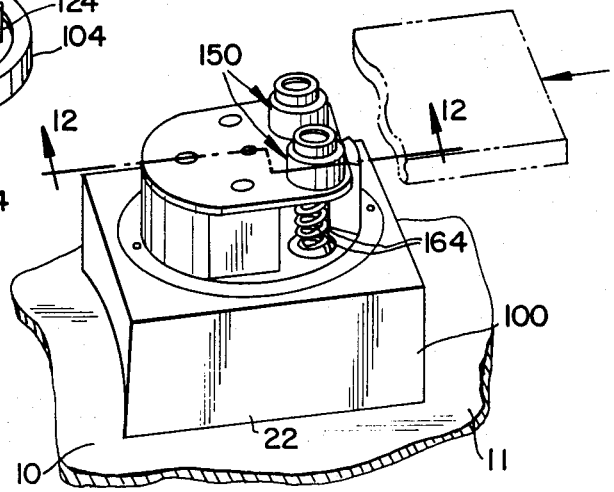
FIG. 11 is an enlarged perspective view of the injector valve assembly.

As seen from FIGS. 9 and 11, there are a pair of cell piercing assemblies 150 circumferentially spaced from each other on the housing section 102.

Operation

When the system of the invention is to be employed, articles to be sterilized are placed within the chamber 10 through the opening covered by the door 12, after which the door is securely closed. A cassette 18 containing a fresh cell pack 28 is selected to be manually inserted into the injector mechanism 20. Before the cassette is inserted the indicator strips 47 and 67 are observed to see whether they indicate that any of the cells are leaking hydrogen peroxide. If a leak exists, the indicator strip on the leak side will have a color indicating such condition, and the cassette should not be used. If the cassette is in proper condition, the strip 67 is removed by way of a suitable pull tab 67c and the cassette is inserted.

As the cassette is being inserted, a number of events occur. The sensor 99 aligned with the edge of the cassette detects the presence of the cassette. A signal from the control 21 starts the motor 95 to rotate the drive roller 94 in a direction to move the cassette into the mechanism. As the cassette is driven in the bar code 66 is read by the sensor 98 by way of the slot 54 and the information transmitted to the control 21. If the cassette is inserted backwards or inverted, the absence of bar code information will cause the mechanism not to accept the cassette. If the cassette is properly oriented but the strip 67 has not been removed, only a portion of the code is seen through the window 69 in the strip 67, causing the solenoid 97 to release the pawl 96 and causing the motor 95 to reverse direction to eject the cassette.

The bar code indicates the nature of the fluid in the cassette, which is necessary since cassettes containing different sterilants or sterilants of differing volumes may be utilized with the apparatus of the invention. Also, the bar code will tell the date on which the sterilant pack 28 has been filled. If wrong material is used or the date is beyond an acceptable shelf life for the material, the dispensing mechanism will eject the cassette as above, and the control 21 will cause to be provided a suitable warning to indicate to the operator that a new cassette should be utilized Assuming the cassette is acceptable, the motor will continue to drive the cassette into the mechanism. As the cassette reaches a fully inserted position, the sensor 99 detects the cassette interruption at the hole 68 in the edge of the cassette. The sensor 99 signals the motor 95 to stop and reverse its direction causing the drive roller 94 to rotate in a direction to move the cassette a short distance out of the mechanism, to position the cassette so that the first cell 30 on the trailing end of the cassette is properly aligned to be pierced. The spring loaded pawl 96 permits such movement until it encounters the grooves 64. The cassette is stopped by the pawl one station before the first cell. The detector 98 senses whether the foil 62 in the opening 52 associated with the first cell to be utilized is still intact. If the foil has been broken, the cassette will be advanced to the next cell. The foil will again be examined and the process repeated as necessary until an interact cell is located or the entire cassette is ejected. Assuming the foil is intact, the cassette is then advanced to the first cell position.

Before the hydrogen peroxide is injected, a vacuum is applied to the chamber 10 by way of the conduit 14. To initiate the fluid injection process, pressurized fluid is applied through the conduit 87 to extend the actuator rod 85 and thereby move the cam 84 from its position wherein its surface 84a is engaging the roller 82 onto the sloping cam section 84b and then into the section 84c.

Figure 13:
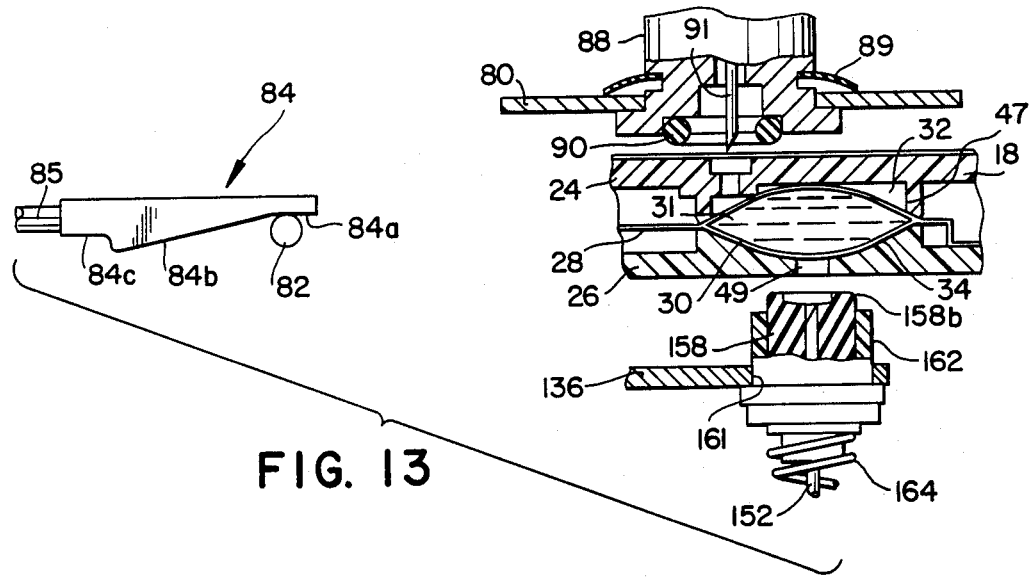
FIGS. 13, 14 and 15 are schematic views of the fluid injection system in operation.
Figure 14:
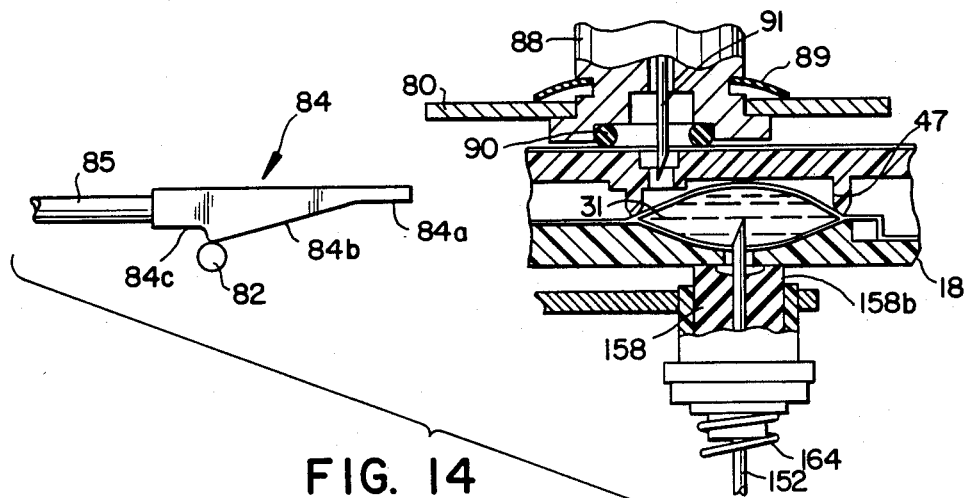

Before the cam movement starts, the cassette 18 and the adjacent components are positioned, as indicated schematically in FIG. 13. There is some clearance between the cassette 18 and the adjacent sealing members, and the needles 91 and 152 have not penetrated the cassette. Movement of the cam to a position wherein the lowest portion of the cam slope 84b is engaging the roller 82 as seen in FIG. 14, forces the clamp plate 76 downwardly, which in turn presses the saddle 80 downwardly moving the clamp 88 into engagement with the upper surface of the cassette 18. This downward movement occurs against the upward forces of the springs 74 and 78. Also, as the lower surface of the cassette engages the upper sealing ring 158b of the seal 158, that seal is moved downwardly against the force of the spring 164.

Several functions have occurred as a result of this downward movement. The O-ring 90 on the top side of the cassette, has been compressed against the cassette to create a seal in that location. That O-ring, of course, surrounds the aperture 46. Also, the needle 91 has pierced the indicator strip 47 and partially entered the aperture 46. Thus, the needle 91 is in communication with the compartment 42 including the space above the pressure side 32 of the cell. The sealing ring 158b surrounds a hole 49 leading to a cell 30, in the lower surface of a cassette to create a seal at that location by compression of the ring 158b. Further, the seal member has been moved downwardly sufficiently far that the needle 152 extends upwardly into the hole 49 and pierces the delivery side 34 of the cell 30. The internal seal 158c on the lower end of the seal member slides on the needle 152 but maintains a seal at that location.

Since a pair of cell piercing assemblies are provided, the cassette has also been moved onto the other piercing assembly 150. This creates a seal in that area and the needle 152b harmlessly extends into the socket 50. Also, a blade 168 positioned on the frame 70 adjacent the lower side of the cassette along one edge is aligned to enter the hole 52 and rupture the foil 62 to provide an indication that the cell associated with that hole has been pierced.

Figure 15:
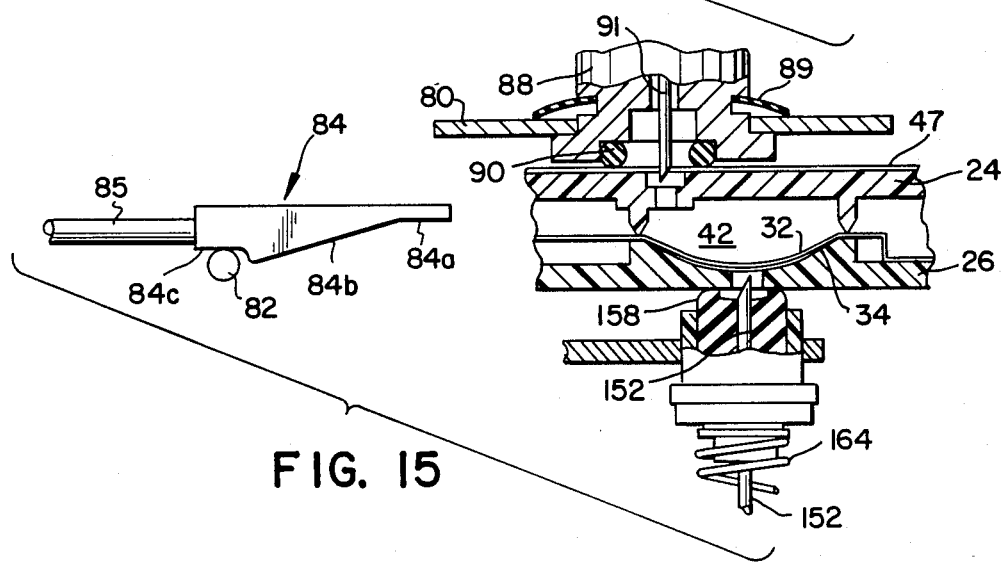

Continued extension of the actuator rod 85 moves the cam 84 off the section 84b onto the section 84c which does not depend as far as the section 84b as indicated schematically in FIG. 15. This allows the spring 74 to urge the platen 72 and the cassette 18 to return upwardly a small amount, which is sufficient to move the cassette away from the needle 152 so that it no longer is extending into the cell 30. The seals produced around the hole 49 and the aperture 46 in the cassette remain intact, however, since the cassette is still under downward pressure.

Movement of the cam to its fully extended position actuates a suitable sensor (not shown) to initiate the flow of pressurized air through the flexible conduit 93 through the needle 91 into the compartment 42 creating pressure against the pressure side 32 of the cell, forcing it downwardly against the fluid 31 in the cell. The fluid is thus forced out of the cell through the hole 49 and into the needle 152. The pressure side 32 of the cell fully inverts against the inner surface of the delivery side 34 of the cell so that the entire volume of fluid within the cell is forced out of it. The outlet from the cell is formed at its lowermost point so that all of the liquid contained in the cell is emptied even if air is present in the cell. Fluid flowing out of the cell 30 is forced downwardly through the needle 152 through the opening 113 in the diaphragm 112, through the radial passage 120 into the valve inlet recess 116 surrounding the valve seat 110.

The pressure applied by the pneumatic air pressure against the pressure side 32 of the cell is sufficient to overcome the valve closing force on the diaphragm 112, which includes the downwardly urging force of the injector valve spring 132, the ambient air pressure, and also the small effect of the vacuum applied to the central downstream side of the diaphragm. It should be noted that the area of the diaphragm receiving the inlet pressure is relatively large. The diaphragm 112 moves away from the valve seat 110 so that fluid can flow through the outlet passage 111 and the nozzle 140 into the chamber 10. This injection of the fluid takes place very quickly, and as soon as the fluid has been injected, the spring 132 immediately reacts against the piston 130 to move the valve element once more into its normal valve-closed position. Although the passages on the upstream side of the valve seat are properly sealed, it is desirable to positively close the valve as quickly as possible so as to minimize the possibilities of the vacuum in the chamber being affected.

The air pressure through the flexible conduit 93 is then withdrawn, and the cam 84 is retracted. The detector 98 has observed through a hole 52 that the next cell in line has not been used. Thus, the solenoid 97 is actuated to release the pawl 96, and the motor 95 is energized to cause the roller 94 to move the cassette outwardly one position, at which time the pawl 96 once more engages a groove 64 to hold the cassette in proper position for the next cycle.

It should be appreciated that the fluid in the cell 30 was positively and quickly injected into the chamber with volumetric accuracy. The only fluid not injected is that remaining in the fluid passages between the cell wall 32 and the valve seat 110. This quantity is very small in relation to the volume of the cell 30, even though the cell volume is small. Moreover, this dead volume is only for the first cell, in that injection of the fluid in the second cell will inject most of this small remaining amount and leave a similar remaining amount, so that volumetric accuracy is obtained.

The next step in the sterilizing cycle is that the injected hydrogen peroxide is allowed to permeate onto all the surfaces of the items being sterilized, and electrical energy forming a plasma is eventually applied. Further details regarding such process are set forth in the above-referenced patent. The cassette and the fluid dispensing mechanism are in position to repeat the cycle upon receipt of an appropriate signal applied to the actuator which moves the cam. All of the cells within a cassette can be sequentially used in this manner. The microprocessor 21 controlling the operation counts the cells as they are used, and when all have been used, the spent cassette is automatically ejected. Alternatively, the absence of foil in a hole 68 can be used to indicate that all of the cells within the cassette have been used.

While the invention has been described in connection with injecting liquid into a chamber for a sterilizing cycle, it should be understood that the system is useful for injecting any type of liquid into a chamber. Further, the injection does not have to be in connection with a sterilizing cycle. Also, the injection system can be useful for injecting liquids into containers other than vacuumized chambers, although the injector valve is particularly useful in connection with a vacuum chamber.

Although the preferred form of the cassette and the dispensing from the cell has been described above, there are, of course, other alternatives. For example, the cell piercing element need not be a tubular needle. Instead, liquid could flow around a puncture element. Also, the need for such an element can be eliminated by bursting a cell. Referring to FIG. 7a, a cell delivery wall 34a is formed with a weakened or thinned central section 34b that will burst or rupture at a predetermined pressure. In addition to eliminating the piercing tip, the corresponding seal needs and cassette positioning steps can be simplified. The wall section 34b can be formed by coining a regular wall or by forming the wall thinner. Related to the foregoing, the wall 34 can be eliminated by forming and filling a cell using the wall 39 as the bottom wall of the cell and forming a thin section at the outlet location that is either pierced or burst. Also alternatively, the section 34b may be a separate layer bonded to the cassette wall 39.

What is claimed is:

1. A fluid coupling and injector valve assembly for use in a fluid injection system, comprising:
   a lower housing section having an annular valve seat surrounding an outlet passage through the section and having a recess in said section around said valve seat forming an inlet;
   a flexible valve element cooperating with said valve seat to control flow through the valve seat, said element also covering said recess such that fluid pressure in said recess urges said flexible element away from said valve seat so as to allow fluid flow from said recess into said valve outlet passage;
   an upper housing section cooperating with said lower section to clamp said element between said sections;
   a spring urging said element into a normally closed position with respect to said valve seat;
   inlet passage means in said upper section for ducting pressurized fluid into said inlet to move said valve element away from said valve seat and allow fluid to flow through said valve when the fluid inlet pressure applied to said element is sufficient to overcome the valve closing force on said element;
   seal means cooperating with said inlet passage means and adapted to form a seal with a fluid supply component when fluid is conducted to said valve inlet; and
   said inlet passage includes a cell piercing needle extending upwardly to pierce said fluid supply component.

2. The assembly of claim 1, wherein said seal means includes a tubular seal member surrounding a piercing end of said needle, said seal member having an axial end face adapted to form a seal with said fluid supply component, said seal member being retractable when compressed against said component to allow said needle end to extend beyond said member and pierce a fluid containing cell within said component.

3. A fluid coupling and injector valve assembly for use in a fluid injection system, comprising:
   a lower housing section having an annular valve seat surrounding an outlet passage through the section and having a recess in said section around said valve seat forming an inlet;
   a flexible valve element cooperating with said valve seat to control flow through the valve seat, said element also covering said recess such that fluid pressure in said recess urges said flexible element away from said valve seat so as to allow fluid flow from said recess into said valve outlet passage;

an upper housing section cooperating with said lower section to clamp said element between said sections;

a spring urging said element into a normally closed position with respect to said valve seat;

inlet passage means including a tubular conduit in said upper section for ducting pressurized fluid into said inlet to move said valve element away from said valve seat and allow fluid to flow through said valve when the fluid inlet pressure applied to said element is sufficient to overcome the valve closing force on said element; and seal means cooperating with said inlet passage means and including a seal on the upper end of said conduit adapted to sealingly engage a fluid supply component when fluid is conducted to said valve inlet wherein said seal is a resilient tubular member slideably mounted on said conduit, and including a spring biasing said tubular member upwardly beyond the end of said conduit, while being retractable when compressed against said fluid supply component.

4. A fluid coupling and injector valve assembly for use in a fluid injection system, comprising:

a lower housing section having an annular valve seat surrounding an outlet passage through the section and having a recess in said section around said valve seat forming an inlet;

a flexible valve element cooperating with said valve seat to control flow through the valve seat, said element also covering said recess such that fluid pressure in said recess urges said flexible element away from said valve seat so as to allow fluid flow from said recess into said valve outlet passage;

an upper housing section cooperating with said lower section to clamp said element between said sections;

a spring urging said element into a normally closed position with respect to said valve seat;

inlet passage means including a tubular conduit in said upper section for ducting pressurized fluid into said inlet to move said valve element away from said valve seat and allow fluid to flow through said valve when the fluid inlet pressure applied to said element is sufficient to overcome the valve closing force on said element; and seal means cooperating with said inlet passage means and including a seal on the upper end of said conduit adapted to sealingly engage a fluid supply component when fluid is conducted to said valve inlet wherein said conduit is fixed to said upper section and said seal extends beyond the upper end of said upper housing section.

5. A fluid coupling and injector valve assembly for use in a fluid injection system, comprising:

a lower housing section having an annular valve seat surrounding an outlet passage through the section and having a recess in said section around said valve seat forming an inlet;

a flexible valve element cooperating with said valve seat to control flow through the valve seat, said element also covering said recess such that fluid pressure in said recess urges said flexible element away from said valve seat so as to allow fluid flow from said recess into said valve outlet passage;

an upper housing section cooperating with said lower section to clamp said element between said sections;

a spring urging said element into a normally closed position with respect to said valve seat;

inlet passage means including a tubular conduit in said upper section for ducting pressurized fluid into said inlet to move said valve element away from said valve seat and allow fluid to flow through said valve when the fluid inlet pressure applied to said element is sufficient to overcome the valve closing force on said element; and seal means cooperating with said inlet passage means and including a seal on the upper end of said conduit adapted to sealingly engage a fluid supply component when fluid is conducted to said valve inlet wherein said conduit has a very small diameter so as to minimize the volume of the passages leading to said valve seat, and the upper end of said seal has a considerably larger diameter to surround a fluid outlet in said component.

* * * * *